(12) United States Patent
Yamamoto (10) Patent No.: US 11,373,307 B2
(45) Date of Patent: Jun. 28, 2022

(54) ULTRASOUND DIAGNOSTIC APPARATUS AND METHOD FOR CONTROLLING ULTRASOUND DIAGNOSTIC APPARATUS

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 944 days.

(21) Appl. No.: 16/146,176

(22) Filed: Sep. 28, 2018

(65) Prior Publication Data

US 2019/0035079 A1    Jan. 31, 2019

Related U.S. Application Data

(63) Continuation of application No. PCT/JP2017/011692, filed on Mar. 23, 2017.

(30) Foreign Application Priority Data

Apr. 1, 2016 (JP) .............................. JP2016-074338

(51) Int. Cl.
*G06T 7/00* (2017.01)
*A61B 8/08* (2006.01)
(Continued)

(52) U.S. Cl.
CPC ............ *G06T 7/0014* (2013.01); *A61B 8/085* (2013.01); *A61B 8/145* (2013.01); *A61B 8/4488* (2013.01);
(Continued)

(58) Field of Classification Search
CPC ......... G06T 7/0014; G06T 2207/10132; G06T 2207/30004; A61B 8/145; A61B 8/4488; G06K 9/6201
See application file for complete search history.

(56) References Cited

U.S. PATENT DOCUMENTS 6,221,020 B1 *   4/2001   Lysyansky ........... G01S 7/52066
                                                          600/453
2005/0238216 A1   10/2005   Yoden
(Continued)

FOREIGN PATENT DOCUMENTS

JP           4-224738 A      8/1992
JP       2005-218796 A       8/2005
(Continued)

OTHER PUBLICATIONS

International Preliminary Report on Patentability and Written Opinion of the International Searching Authority(Forms PCT/IB/326, PCT/IB/373 and PCT/ISA/237), dated Oct. 11, 2018, for International Application No. PCT/JP2017/011692, with an English Translation of the Written Opinion.

(Continued)

*Primary Examiner* — Rochelle D Turchen
(74) *Attorney, Agent, or Firm* — Birch, Stewart, Kolasch & Birch, LLP (57) ABSTRACT

An ultrasound diagnostic apparatus includes: an array transducer in which a plurality of elements are arranged; a transmitting unit that transmits an ultrasound beam to a subject; a receiving unit that receives ultrasound echoes from the subject to acquire element data; an element data analysis unit that analyzes the element data to acquire element data information; a collation pattern database in which a plurality of collation patterns that are associated with a plurality of examination parts of the subject and are related to the element data information are stored in advance; and a part recognition unit that collates the element data information using the collation pattern to perform part recognition determining from which examination part of the subject the ultrasound echoes have been reflected.

19 Claims, 7 Drawing Sheets

(51) Int. Cl.
*A61B 8/14* (2006.01)
*A61B 8/00* (2006.01)
*G06K 9/62* (2022.01)

(52) U.S. Cl.
CPC .......... *A61B 8/5207* (2013.01); *A61B 8/5215* (2013.01); *A61B 8/5223* (2013.01); *G06K 9/6201* (2013.01); *G06T 2207/10132* (2013.01); *G06T 2207/30004* (2013.01)

(56) References Cited

U.S. PATENT DOCUMENTS

| | | | | |
|---|---|---|---|---|
| 2009/0080711 | A1* | 3/2009 | Yokoi | G06K 9/629 382/116 |
| 2016/0287214 | A1* | 10/2016 | Ralovich | G16H 50/20 |

FOREIGN PATENT DOCUMENTS

| | | | |
|---|---|---|---|
| JP | 2007-117351 A | 5/2007 | |
| JP | 4794292 B2 | 10/2011 | |

OTHER PUBLICATIONS

International Search Report (Form PCT/ISA/210), dated Jun. 13, 2017, for International Application No. PCT/JP2017/011692, with an English translation.

* cited by examiner

ULTRASOUND DIAGNOSTIC APPARATUS AND METHOD FOR CONTROLLING ULTRASOUND DIAGNOSTIC APPARATUS

CROSS-REFERENCE TO RELATED APPLICATIONS

This application is a Continuation of PCT International Application No. PCT/JP2017/011692 filed on Mar. 23, 2017, which claims priority under 35 U.S.C. § 119(a) to Japanese Patent Application No. 2016-074338 filed on Apr. 1, 2016. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more particularly, to an ultrasound diagnostic apparatus that recognizes an examination part of a subject.

2. Description of the Related Art

In the related art, an ultrasound diagnostic apparatus using an ultrasound image has been put to practical use in the medical field. In general, in this type of ultrasound diagnostic apparatus, an array transducer in which a plurality of elements are arranged scans a subject with an ultrasound beam and receives ultrasound echoes from the subject to acquire element data. The ultrasound diagnostic apparatus electrically processes the element data to generate an ultrasound image.

In a case in which the ultrasound diagnostic apparatus is used to diagnose a plurality of examination parts of the subject, appropriate imaging conditions that vary depending on an examination part are present in order to obtain ultrasound images suitable for diagnosis for each examination part. For example, JP1992-224738A (JP-H04-224738A) discloses an ultrasound diagnostic apparatus which generates an ultrasound image using acquired element data, automatically recognizes an imaging part in the generated ultrasound image using a pattern matching process, and sets a scanning parameter suitable for the imaging part on the basis of the recognition result.

SUMMARY OF THE INVENTION

However, as in the apparatus disclosed in JP1992-224738A (JP-H04-224738A), in a case in which the ultrasound image is generated using the acquired element data, phasing addition is performed for each element data item for a reception focusing process and the information of the spatial spreading of sound waves included in the element data is lost. Therefore, in a case in which the imaging part is recognized from the generated ultrasound image by the pattern matching process, the accuracy of recognition is reduced by a value corresponding to the lost information and there is a concern that an error will occur in the recognition of the imaging part. As such, in a case in which an error occurs in part recognition, it is difficult to appropriately set the scanning parameters, which is likely to hinder diagnosis.

The invention has been made in order to solve the problems of the related art and an object of the invention is to provide an ultrasound diagnostic apparatus and a method for controlling the ultrasound diagnostic apparatus that can improve the accuracy of part recognition.

According to the invention, there is provided an ultrasound diagnostic apparatus comprising: an array transducer in which a plurality of elements are arranged; a transmitting unit that transmits an ultrasound beam from the array transducer to a subject; a receiving unit that receives ultrasound echoes from the subject using the array transducer to acquire element data; an element data analysis unit that analyzes the element data acquired by the receiving unit to acquire element data information; a collation pattern database in which a plurality of collation patterns that are associated with a plurality of examination parts of the subject and are related to the element data information are stored in advance; and a part recognition unit that reads the collation pattern from the collation pattern database and collates the element data information acquired by the element data analysis unit using the read collation pattern to perform part recognition determining from which examination part of the subject the ultrasound echoes have been reflected.

Preferably, the ultrasound diagnostic apparatus further comprises an element data memory that sequentially stores the element data acquired by the receiving unit. Preferably, the element data analysis unit analyzes the element data stored in the element data memory to acquire the element data information.

The ultrasound diagnostic apparatus may further comprise an image generation unit that generates an ultrasound image of the subject using the element data. Preferably, a part recognition process of the part recognition unit and a process of generating the ultrasound image by the image generation unit are performed in parallel.

The number of scanning lines corresponding to each element data item for acquiring the element data information used for the part recognition by the part recognition unit may be less than the number of scanning lines corresponding to each element data item used for the generation of the ultrasound image by the image generation unit.

The scanning lines corresponding to each element data item for acquiring the element data information used for the part recognition by the part recognition unit may be thinned out at a predetermined interval in a direction in which the plurality of elements are arranged, with respect to the scanning lines corresponding to each element data item used for the generation of the ultrasound image by the image generation unit.

The element data analysis unit may further acquire the element data information including information of frequency characteristics. In addition, the element data analysis unit may further acquire the element data information including information of an amplitude.

The transmitting unit may transmit the ultrasound beam to a plurality of different focuses. The element data analysis unit may acquire each element data information item for the plurality of focuses. The part recognition unit may collate each element data information item for the plurality of focuses, using the collation pattern.

The element data analysis unit may analyze a plurality of element data items output from the plurality of elements that have received the ultrasound echoes reflected in the vicinity of each focus to acquire the element data information.

The ultrasound diagnostic apparatus may further comprise an imaging condition setting unit that sets image generation conditions corresponding to an examination part of the subject recognized by the part recognition unit. The image generation unit may generate the ultrasound image according to the image generation conditions set by the imaging condition setting unit.

The imaging condition setting unit may further set ultrasound beam transmission conditions corresponding to the examination part of the subject recognized by the part recognition unit and the transmitting unit may transmit the ultrasound beam according to the ultrasound beam transmission conditions set by the imaging condition setting unit.

According to the invention, there is provided a method for controlling an ultrasound diagnostic apparatus. The method comprises: a step of transmitting an ultrasound beam from an array transducer in which a plurality of elements are arranged to a subject; a step of receiving ultrasound echoes from the subject using the array transducer to acquire element data; a step of analyzing the acquired element data to acquire element data information; and a step of collating the element data information using a plurality of collation patterns that are associated with a plurality of examination parts of the subject to perform part recognition determining from which examination part of the subject the ultrasound echoes have been reflected.

According to the invention, an ultrasound beam is transmitted from the array transducer in which a plurality of elements are arranged to the subject. The array transducer receives the ultrasound echoes from the subject to acquire element data. The acquired element data is analyzed to acquire element data information. The element data information is collated using a plurality of collation patterns associated with a plurality of examination parts of the subject to perform part recognition determining from which examination part of the subject the ultrasound echoes have been reflected. Therefore, it is possible to improve the accuracy of part recognition.

DESCRIPTION OF THE PREFERRED EMBODIMENTS

Hereinafter, embodiments of the invention will be described with reference to the accompanying drawings.

Embodiment 1

Figure 1:
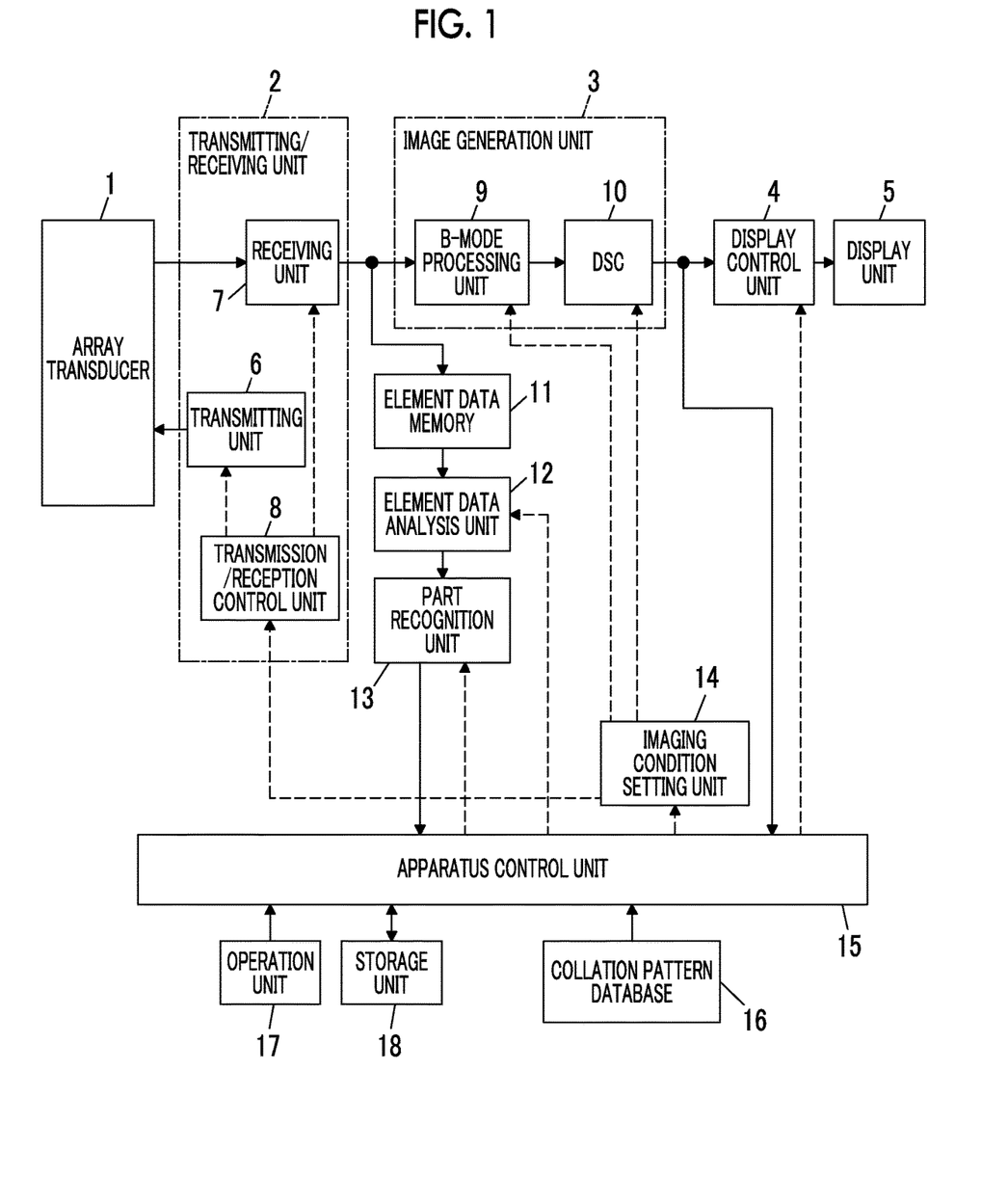
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. The ultrasound diagnostic apparatus includes an array transducer 1. An image generation unit 3 is connected to the array transducer 1 through a transmitting/receiving unit 2 and a display unit 5 is connected to the image generation unit 3 through a display control unit 4.

The transmitting/receiving unit 2 includes a transmitting unit 6 and a receiving unit 7 that are connected to the array transducer 1 and a transmission/reception control unit 8 that is connected to the transmitting unit 6 and the receiving unit 7. The image generation unit 3 includes a brightness-mode (B-mode) processing unit 9 that is connected to the receiving unit 7 of the transmitting/receiving unit 2 and a digital scan converter (DSC) 10 that is connected to the B-mode processing unit 9. The display control unit 4 is connected to the DSC 10.

An element data memory 11, an element data analysis unit 12, and a part recognition unit 13 are sequentially connected in series to the receiving unit 7 of the transmitting/receiving unit 2.

In addition, an imaging condition setting unit 14 is connected to the transmission/reception control unit 8 of the transmitting/receiving unit 2 and the B-mode processing unit 9 and the DSC 10 of the image generation unit 3.

An apparatus control unit 15 is connected to the display control unit 4, the DSC 10, the element data analysis unit 12, the part recognition unit 13, and the imaging condition setting unit 14. In addition, a collation pattern database 16, an operation unit 17, and a storage unit 18 are connected to the apparatus control unit 15.

The array transducer 1 includes a plurality of elements (ultrasound transducers) that are one-dimensionally or two-dimensionally arranged. Each of the elements transmits ultrasonic waves in response to a driving signal supplied from the transmitting unit 6. In addition, each of the elements receives ultrasound echoes from a subject and outputs a received signal. Each element is, for example, a transducer in which electrodes are formed at both ends of a piezoelectric body made of piezoelectric ceramic typified by lead zirconate titanate (PZT), a polymer piezoelectric element typified by polyvinylidene difluoride (PVDF), or a piezoelectric crystal typified by lead magnesium niobate-lead titanate (PMN-PT).

In a case in which a pulsed voltage or a continuous-wave voltage is applied to the electrodes of the transducer, the piezoelectric body is expanded and contracted and pulsed or continuous ultrasonic waves are generated from each transducer. The ultrasonic waves are combined to form an ultrasound beam. In addition, each transducer receives propagated ultrasonic waves, is expanded and contracted, and generates an electric signal. The electric signal is output as a received ultrasound signal.

The transmitting/receiving unit 2 transmits and receives an ultrasound beam according to the set ultrasound beam transmission and reception conditions and the image generation unit 3 generates a B-mode image signal according to the set ultrasound image generation conditions. In addition, imaging conditions include ultrasound beam transmission conditions for the transmitting unit 6 and ultrasound image generation conditions for the image generation unit 3.

The transmitting unit 6 of the transmitting/receiving unit 2 includes, for example, a plurality of pulse generators, adjusts the amount of delay of each driving signal such that the ultrasonic waves transmitted from a plurality of elements in the array transducer 1 form an ultrasound beam, on the basis of a transmission delay pattern selected according to a control signal from the transmission/reception control unit 8, and supplies the driving signals to the plurality of elements.

Figure 2:
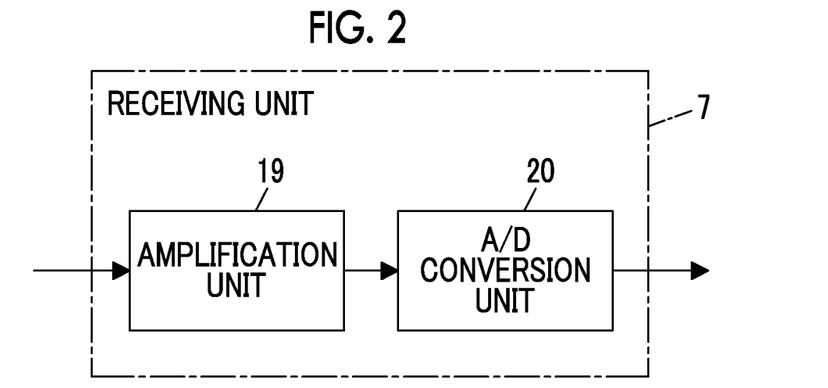
FIG. 2 is a block diagram illustrating the internal configuration of a receiving unit in Embodiment 1.

As illustrated in FIG. 2, the receiving unit 7 has a configuration in which an amplification unit 19 and an analogue/digital (A/D) conversion unit 20 are sequentially connected in series. The receiving unit 7 amplifies the received signals transmitted from each element of the array transducer 1 with the amplification unit 19, converts the received signals into digital signals with the A/D conversion unit 20 to obtain element data, and outputs the element data to the image generation unit 3 and the element data memory 11.

The element data memory 11 sequentially stores the element data output from the receiving unit 7.

The element data analysis unit 12 analyzes the element data stored in the element data memory 11 to acquire element data information included in the element data.

The element data information is two-dimensional data information in which the element data obtained from each element by one ultrasonic wave transmission and reception operation is arranged in the direction in which the elements are arranged and a reception time direction. The element data information includes information of the spatial distribution of sound waves.

A plurality of collation patterns related to the element data information are stored in the collation pattern database 16 in advance. The collation patterns are associated with each of a plurality of examination parts of the subject.

The part recognition unit 13 reads the collation pattern related to the element data information from the collation pattern database 16, collates the element data information acquired by the element data analysis unit 12 using the read collation pattern, and performs part recognition determining from which examination part of the subject the ultrasound echoes have been reflected.

The imaging condition setting unit 14 stores imaging conditions corresponding to a plurality of examination parts in advance and sets imaging conditions corresponding to the examination part recognized by the part recognition unit 13.

The transmission/reception control unit 8 controls the transmitting unit 6 and the receiving unit 7 on the basis of various control signals transmitted from the apparatus control unit 15 such that the transmission of ultrasound pulses to the subject and the reception of ultrasound echoes from the subject are repeated at a pulse repetition frequency (PRF) interval.

Figure 3:
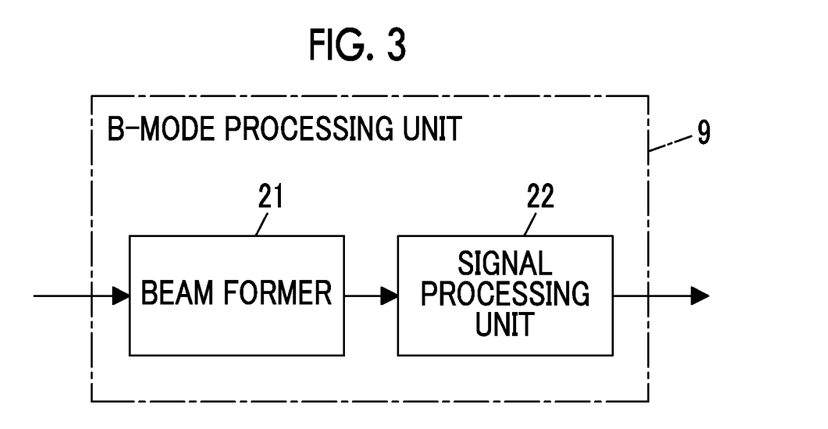
FIG. 3 is a block diagram illustrating the internal configuration of a B-mode processing unit in Embodiment 1.

The B-mode processing unit 9 of the image generation unit 3 has a configuration in which a beam former 21 and a signal processing unit 22 are sequentially connected in series, as illustrated in FIG. 3. The beam former 21 applies a delay to each element data item output from the receiving unit 7 of the transmitting/receiving unit 2 according to a sound speed or a sound speed distribution set on the basis of a reception delay pattern selected according to a control signal from the imaging condition setting unit 14 and adds the received element data to perform a reception focusing process. A sound ray signal in which the focus of an ultrasound echo subjected to phasing addition is narrowed is generated by the reception focusing process.

The signal processing unit 22 corrects the attenuation of the sound ray signal generated by the beam former 21 depending on a distance according to the depth of the reflection position of ultrasonic waves and then performs an envelope detection process. In addition, the signal processing unit 22 performs various types of necessary image processing including a gradation process to generate a B-mode image signal which is tomographic image information related to the tissues of the subject.

The DSC 10 of the image generation unit 3 converts the B-mode image signal generated by the signal processing unit 22 into an image signal based on a general television signal scanning system (raster conversion) and outputs the image signal to the display control unit 4 and the apparatus control unit 15.

The image generation unit 3 performs the process of generating the B-mode image signal in parallel to the part recognition process of the part recognition unit 13.

The display control unit 4 displays a B-mode image on the display unit 5 on the basis of the B-mode image signal generated by the image generation unit 3.

The display unit 5 includes a display device, such as a liquid crystal display (LCD), and displays the B-mode image under the control of the display control unit 4.

The operation unit 17 is used by a user to perform an input operation and may include, for example, a keyboard, a mouse, a trackball, and a touch panel.

The apparatus control unit 15 determines whether an imaging part of the subject has been changed on the basis of the B-mode image signal generated by the image generation unit 3.

In addition, the apparatus control unit 15 controls the display control unit 4, the element data analysis unit 12, the part recognition unit 13, and the imaging condition setting unit 14 on the basis of commands input from the user through the operation unit 17.

The storage unit 18 stores, for example, an operation program. For example, a recording medium, such as a hard disk, a flexible disk, a magneto-optical disk (MO), a magnetic tape (MT), a random access memory (RAM), a compact disk read only memory (CD-ROM), a digital versatile disk read only memory (DVD-ROM), a secure digital card (SD card), a compact flash card (CF card), or a universal serial bus memory (USB memory), or a server may be used as the storage unit 18.

The image generation unit 3, the display control unit 4, the transmission/reception control unit 8 of the transmitting/receiving unit 2, the element data memory 11, the element data analysis unit 12, the part recognition unit 13, the imaging condition setting unit 14, and the apparatus control unit 15 are formed by a central processing unit (CPU) and an operation program that causes the CPU to perform various processes. However, these units may be formed by digital circuits. In addition, some or all of the image generation unit 3, the display control unit 4, the transmission/reception control unit 8 of the transmitting/receiving unit 2, the element data memory 11, the element data analysis unit 12, the part recognition unit 13, the imaging condition setting unit 14, and the apparatus control unit 15 may be integrated into one CPU.

Figure 4:
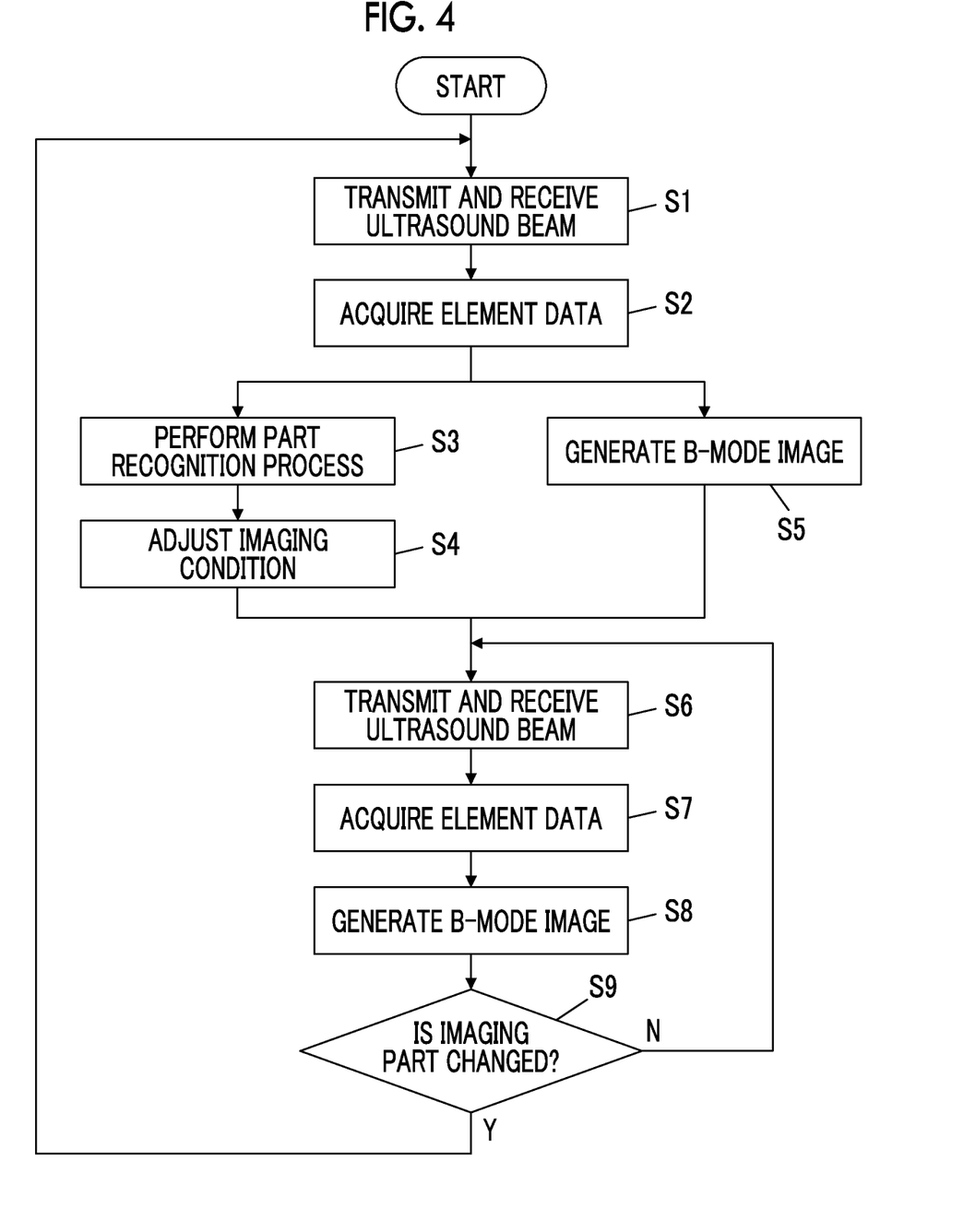
FIG. 4 is a flowchart illustrating the operation of Embodiment 1.

Next, the operation of Embodiment 1 will be described with reference to a flowchart illustrated in FIG. 4.

Figure 5:
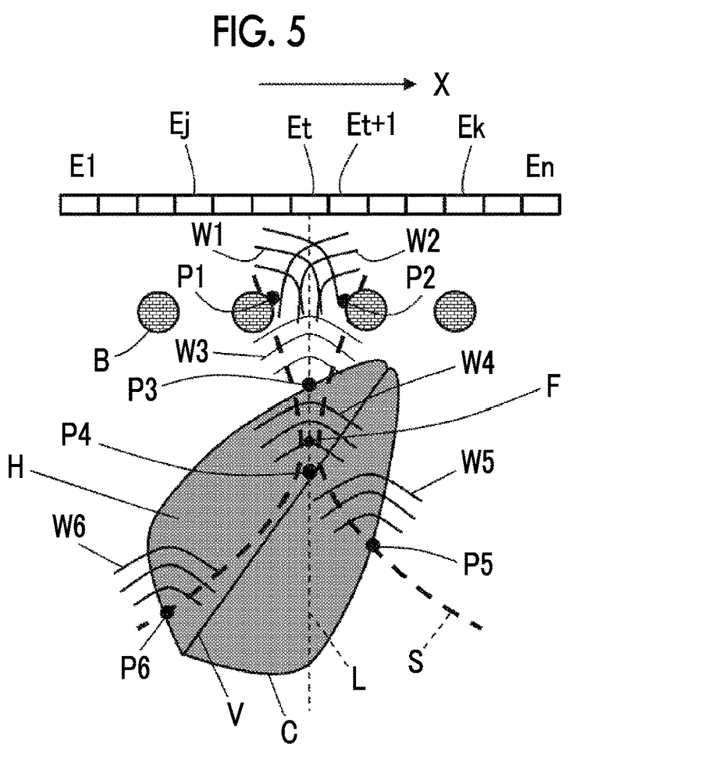
FIG. 5 is a diagram illustrating ultrasound beams which are transmitted from each element into a subject and reflected waves which are generated from reflection points in the subject and travel to each element.

First, in Step S1, a plurality of elements of the array transducer 1 transmit and receive ultrasonic waves to and from the subject. Specifically, as illustrated in FIG. 5, the transmitting unit 6 of the transmitting/receiving unit 2 supplies a driving signal to a plurality of elements E1 to En (where n is an integer equal to or greater than 2) of the array transducer 1. Then, the plurality of elements E1 to En transmit an ultrasound beam S to a focus F that is located on a scanning line L passing through an element Et. Here, t is an integer in the range of 1 to n.

All of the plurality of elements E1 to En may not be driven to transmit the ultrasound beam S. For example, as illustrated in FIG. 5, a plurality of elements Ej to Ek (where j is an integer equal to or greater than 1 and k is an integer that is equal to or less than n and is greater than j) which are some of the plurality of elements E1 to En may be driven to transmit the ultrasound beam S.

In a case in which ultrasound echoes are reflected in the subject, if the ultrasound echoes are reflected from, for example, bones and the boundaries between the organs, the intensity of reflected waves is particularly high. That is, the intensity of reflected waves from a bone B, an outer wall C of the heart H, and a boundary V between the left atrium and the left ventricle and the right atrium and the right ventricle of the heart H in the subject is particularly high.

In this case, the bone B is located at a position that is shallowest from the plurality of elements E1 to En. Therefore, first, particularly strong reflected waves W1 and W2 are reflected from reflection points P1 and P2 above the bone B. Then, the plurality of elements E1 to En receive the reflected wave W1 and the reflected wave W2. Then, a particularly strong reflected wave W3 is reflected from a reflection point P3 on the outer wall C of the heart H which is located at a position deeper than the bone B. A particularly strong reflected wave W4 is reflected from a reflection point P4 on the boundary V which is located at a position deeper than the reflection point P3. The plurality of elements E1 to En receive the reflected wave W3 and the reflected wave W4 in the order of the reflected wave W3 and the reflected wave W4.

In addition, a particularly strong reflected wave W5 is reflected from a reflection point P5 on the outer wall C of the heart H which is located at a position deeper than the reflection point P4. Finally, a particularly strong reflected wave W6 is reflected from a reflection point P6 on the outer wall C of the heart H which is located at a position deeper than the reflection point P5. The plurality of elements E1 to En receive the reflected wave W5 and the reflected wave W6 in the order of the reflected wave W5 and the reflected wave W6. Then, the plurality of elements E1 to En which have received the reflected waves W1 to W6 output the received signals to the receiving unit 7 of the transmitting/receiving unit 2.

All of the plurality of elements E1 to En may not be used to receive the reflected waves W1 to W6. For example, a plurality of elements Ej to Ek which are some of the plurality of elements E1 to En illustrated in FIG. 5 may be used to receive the reflected waves W1 to W6.

Then, in Step S2, the receiving unit 7 generates element data. The generated element data is output from the receiving unit 7 to the element data memory 11 and the image generation unit 3.

As such, in a case in which the ultrasound beam S is transmitted to the focus F located on each scanning line L passing through the element Et, it is possible to generate a plurality of element data items corresponding to a plurality of scanning lines L passing through the plurality of elements E1 to En. The element data output from the receiving unit 7 of the transmitting/receiving unit 2 is sequentially stored in the element data memory 11.

Figure 6:
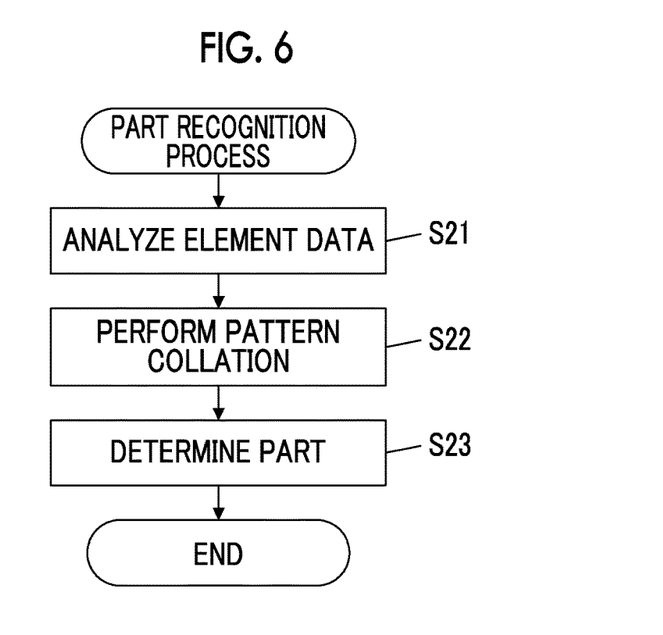
FIG. 6 is a flowchart illustrating a part recognition process.

Then, in Step S3, the part recognition process is performed. Specifically, a process from Step S21 to Step S23 illustrated in a flowchart of FIG. 6 is performed.

Figure 7:
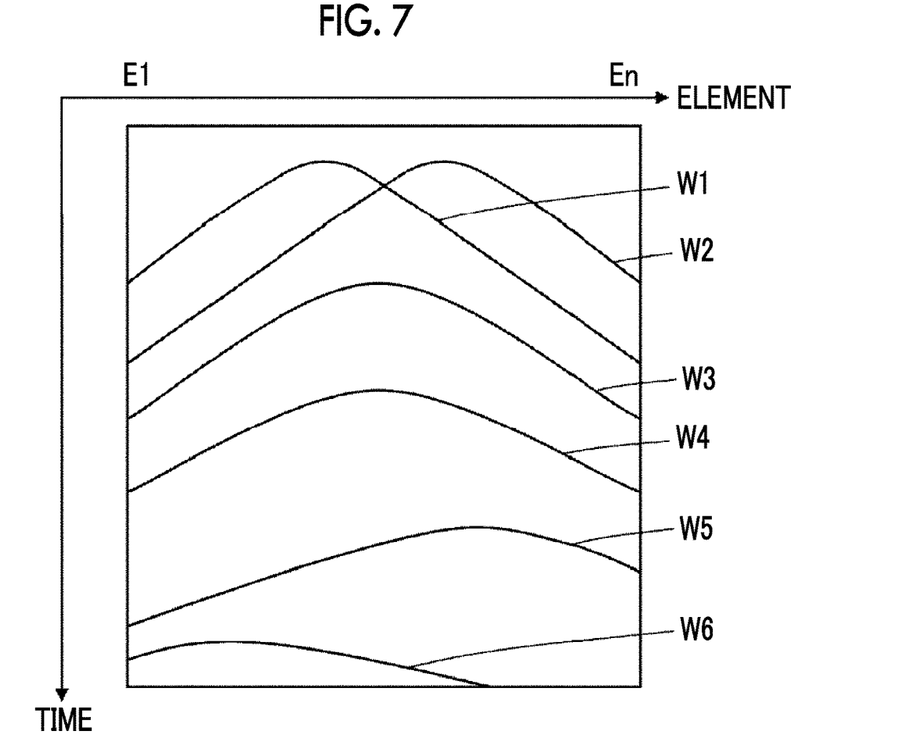
FIG. 7 is a diagram illustrating element data information in Embodiment 1.

First, in Step S21, the element data analysis unit 12 analyzes the element data stored in the element data memory 11 to acquire element data information illustrated in FIG. 7. In the element data information, points with the maximum amplitude in the element data generated by the receiving unit 7 of the transmitting/receiving unit 2 are arranged in the direction in which the plurality of elements E1 to En are arranged and a depth direction, that is, a temporal direction.

As described above, in a case in which the ultrasound beam S is transmitted to the focus F in the subject illustrated in FIG. 5, particularly strong reflected waves W1 to W6 are generated from the bone B, the outer wall C of the heart H, and the boundary V between the left atrium and the left ventricle and the right atrium and the right ventricle of the heart H. Therefore, as illustrated in FIG. 7, the reflected waves W1 to W6 are shown in the element data information. The element data information includes information indicating how the reflected waves W1 to W6 are spatially spread. Therefore, the acquisition of the element data information makes it possible to acquire the information of the spatial spreading of the reflected waves W1 to W6 in the vicinity of the scanning line L in addition to information on the scanning line L illustrated in FIG. 5.

In a case in which a plurality of element data items corresponding to a plurality of scanning lines L passing through the plurality of elements E1 to En are acquired, the element data analysis unit 12 analyzes the element data items to acquire a plurality of element data information items corresponding to the plurality of scanning lines L. In this case, a plurality of element data information items illustrated in FIG. 7, which will be described below, are present.

Then, in Step S22, the part recognition unit 13 collates the element data information acquired by the element data analysis unit 12. It is considered that each of the element data information items acquired by the element data analysis unit 12 has a characteristic pattern according to a plurality of examination parts of the subject. For example, the element data information illustrated in FIG. 7 shows the reflected waves generated from the heart.

Since the element data information includes the information of the spatial spreading of the sound waves as described above, the position of the reflection point from which the reflected wave is reflected in a case in which the ultrasound beam is transmitted is determined by the positional relationship between each examination part and, for example, bones, organs, or blood vessels in the vicinity of each examination part. Therefore, a typical element data information pattern in a case in which the ultrasound beam is transmitted may be prepared in advance for each examination part by, for example, actual measurement or sound wave propagation simulation calculation and the patterns may be used as the collation patterns.

For example, the element data information illustrated in FIG. 7 can be used as the collation pattern related to the element data information corresponding to the heart. The element data information includes information of the reflected wave W1 and the reflected wave W2 generated from the bone B in the vicinity of the heart H as well as the reflected waves W3 to W6 generated from the heart H illustrated in FIG. 5. In a case in which the collation patterns are prepared, not only one collation pattern for one examination part, but also a plurality of collation patterns for one examination part may be prepared in consideration of, for example, the individual difference between the subjects and the body position of the subject in examination. In addition, the collation patterns may be prepared in consideration of a reflected wave which is generated from the outer wall C of the heart H at a position deeper than the position where the reflected wave W5 or the reflected wave W6 is generated, depending on an examination depth, which is not illustrated in FIG. 7.

The collation pattern database 16 stores a plurality of collation patterns related to the element data information in advance. The collation patterns are associated with the examination parts that are generally examined, such as the heart, the liver, the kidney, the gallbladder, the pancreas, the stomach, the lung, the bladder, the thyroid, and the breast.

The part recognition unit 13 reads all of the collation patterns from the collation pattern database 16 and collates the element data information acquired by the element data analysis unit 12 using each of the read collation patterns. In addition, a known matching technique can be used to collate the element data information with the read collation patterns. For example, the element data information may be collated by a cross-correlation function in addition to the matching technique.

For example, in a case in which the result indicating that the element data information is closest to a collation pattern corresponding to the heart among a plurality of read collation patterns is obtained by the above-mentioned methods, the recognition result indicating that the ultrasound echoes have been reflected from the heart is obtained.

The part recognition process can be performed using at least one element data information item. However, in a case in which a plurality of element data information items corresponding to a plurality of scanning lines L are acquired, it is preferable to perform part recognition using the plurality of element data information items in order to improve the accuracy of recognition.

In addition, in a case in which a plurality of element data information items corresponding to the plurality of scanning lines L are acquired, for example, element data information corresponding to the scanning line L passing through the element E1 illustrated in FIG. 5 is different from element data information corresponding to the scanning line L passing through the element En. The reason is that, in a case in which the ultrasound beam S is transmitted to the focuses F on the scanning lines L which deviate from each other in the arrangement direction X of the plurality of elements E1 to En, the reflected waves W1 to W6 from the reflection points P1 to P6 which deviate from each other in the arrangement direction X are received by the plurality of elements E1 to En.

For this reason, it is preferable that the element data information and the collation pattern correspond to the same scanning line L in order to collate the element data information acquired by the element data analysis unit 12. In addition, it is preferable that the widths of the reflected waves W1 to W6 shown in the element data information and the collation patterns in the depth direction and the arrangement direction X are close to each other.

Here, as described above, in a case in which the image generation unit 3 generates a B-mode image signal using the element data output from the receiving unit 7 of the transmitting/receiving unit 2, the reception focusing process is performed. A sound ray signal in which the focus of an ultrasound echo subjected to phasing addition is narrowed is generated by the reception focusing process. For example, the sound ray signal includes only the information of the reflected wave W3 and the reflected wave W4 located on the scanning line L in FIG. 5. That is, in a case in which phasing addition is performed for each element data item for the reception focusing process, the information of the reflected wave W1, the reflected wave W2, the reflected wave W5, and the reflected wave W6 in the vicinity of the scanning line L is lost.

In contrast, the element data information includes the reflected wave W1, the reflected wave W2, the reflected wave W5, and the reflected wave W6 which are information in the vicinity of the scanning line L as well as the reflected wave W3 and the reflected wave W4 which are information on the scanning line L. Therefore, in the part recognition using the element data information, it is possible to improve the accuracy of part recognition by a level corresponding to the information in the vicinity of the scanning line L, as compared to the part recognition using the B-mode image signal.

In Step S23, the part recognition unit 13 determines that the examination part of the subject is the heart on the basis of the recognition result indicating that the ultrasound echoes have been reflected from the heart and outputs the determination result to the apparatus control unit 15. Then, in Step S4 of the flowchart illustrated in FIG. 4, the imaging condition setting unit 14 adjusts the imaging conditions. The imaging condition setting unit 14 stores a plurality of imaging conditions in advance, selects an imaging condition on the basis of the output determination result, and controls the transmitting/receiving unit 2 and the image generation unit 3 such that imaging is performed for the subsequent frames under the selected imaging condition.

In Step S5, a B-mode image signal is generated in parallel to Step S3 and Step S4. That is, the element data output from the receiving unit 7 of the transmitting/receiving unit 2 is input to the image generation unit 3. The B-mode processing unit 9 performs phasing addition for the element data and performs the reception focusing process. The DSC 10 performs signal conversion to generate a B-mode image signal. In a case in which a plurality of element data items corresponding to the plurality of scanning lines L passing through the elements E1 to En are acquired, part recognition is performed using the element data information obtained by one ultrasound transmission and reception operation in Step S3 and Step S4. In Step S5, as much element data as possible is used to generate the B-mode image signal in order to improve the quality of the B-mode image signal. Then, the generated B-mode image signal is output to the display control unit 4 and the apparatus control unit 15 and a B-mode image is displayed on the display unit 5.

As such, since the B-mode image signal generation process in Step S5 is performed in parallel to the part recognition process in Step S3 and the imaging condition adjustment process in Step S4, the time until the imaging condition is adjusted is reduced and it is possible to prevent the delay of the operation of the user and to improve operability. In addition, since the part recognition process and the B-mode image signal generation process are performed in parallel, the calculation time required for these processes is reduced and it is possible to increase a frame rate.

Then, in Step S6, the transmitting unit 6 of the transmitting/receiving unit 2 is controlled according to an ultrasound beam transmission condition included in the imaging condition selected by the imaging condition setting unit 14 and transmits an ultrasound beam. Then, in Step S7, the receiving unit 7 of the transmitting/receiving unit 2 acquires element data. In Step S8, the image generation unit 3 is controlled according to the image generation condition selected by the imaging condition setting unit 14. In addition, the B-mode image signal from the image generation unit 3 is displayed on the display unit 5. Therefore, it is possible to display a B-mode image suitable for the heart on the display unit 5.

Then, in Step S9, the apparatus control unit 15 determines whether the imaging part in the B-mode image signal has been changed.

In a case in which it is determined in Step S9 that the imaging part in the B-mode image signal has not been changed, the process returns to Step S6. Therefore, Steps S6 to S9 are repeated until the apparatus control unit 15 determines that the imaging part in the B-mode image signal has been changed and the heart which is the imaging part is continuously diagnosed.

In contrast, in a case in which it is determined in Step S9 that the imaging part in the B-mode image signal has been changed, the process returns to Step S1. For example, in a case in which the examination part is changed from the heart to the lung and the imaging part is changed, it is determined that the imaging part has been changed. Specifically, in general, in a case in which the imaging part is changed, the array transducer is separated from the surface of the body and emits ultrasonic waves to the air. Therefore, it is possible to determine whether the imaging part has been changed by detecting the aerial emission state (a state in which no reflected signals are obtained).

In a case in which the process returns to Step S1, element data is acquired through Step S1 and Step S2. Then, the part recognition process and the imaging condition adjustment process in Steps S3 and S4 are performed in parallel to the B-mode image generation process in Step S5 and the imaging condition is set. In addition, a B-mode image signal suitable for the lung is generated through Steps S6 to S8. Steps S6 to S9 are repeated to diagnose the changed imaging part.

As described above, in a case in which a plurality of element data items corresponding to a plurality of scanning lines L are acquired, the image generation unit 3 generates a B-mode image signal using as much element data as possible. However, in the part recognition process, the part recognition unit 13 does not necessarily analyze as much element data as possible to acquire the element data information. That is, the part recognition unit 13 may analyze the amount of element data less than the amount of element data used to generate the B-mode image signal to acquire the element data information, may collate the acquired element data information, and may perform the part recognition process.

As illustrated in FIG. 7, in the element data information, the points with the maximum amplitude in the element data are arranged in the temporal direction and the arrangement direction of the plurality of elements E1 to En. Therefore, for example, the comparison between element data corresponding to the scanning line L passing through the element Et illustrated in FIG. 5 and element data corresponding to the scanning line L passing through the element Et+1 shows that there is a difference corresponding to one element between the image data items in the arrangement direction X of the plurality of elements E1 to En and the element data items can be regarded as substantially the same element data.

Figure 8:
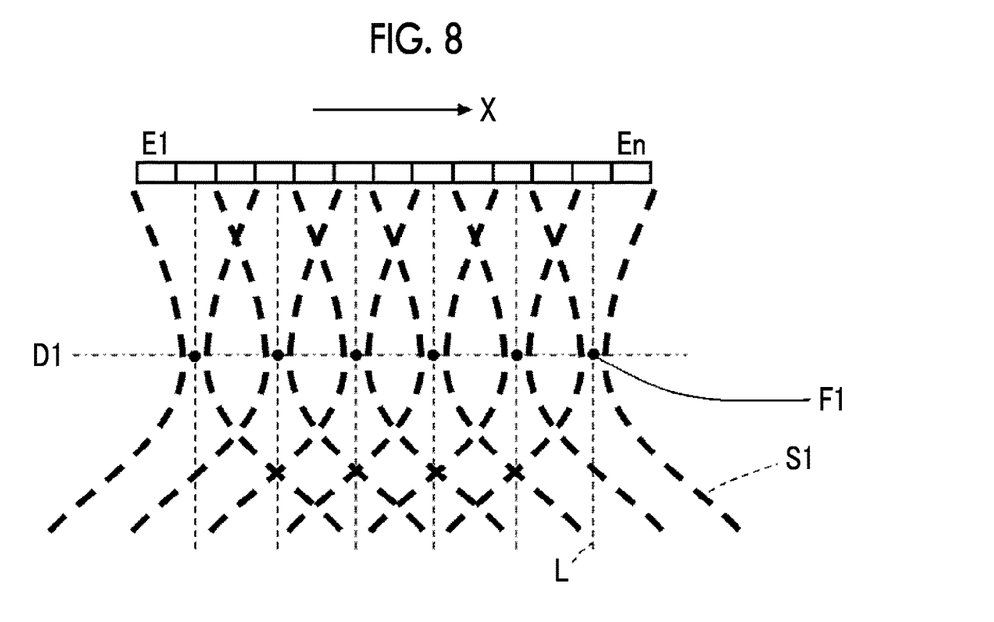
FIG. 8 is a diagram illustrating an aspect in which scanning lines are thinned out in a modification example of Embodiment 1.

Therefore, in the part recognition process of the part recognition unit 13, as illustrated in FIG. 8, the scanning lines L may be thinned out at a predetermined interval of, for example, every two elements in the arrangement direction X and a plurality of element data items corresponding to half the number of scanning lines L may be analyzed to acquire a plurality of element data information items. Since the plurality of element data information items corresponding to half the number of scanning lines L include the information of the spatial spreading of the sound waves as described above, it can be considered that there is little difference between the obtained information and a plurality of element data information items corresponding to the plurality of scanning lines L passing through all of the elements E1 to En.

As such, since the scanning lines L are thinned out at a predetermined interval in the arrangement direction X and a plurality of element data information items corresponding to the thinned-out scanning lines L are acquired, it is possible to reduce the amount of element data required to acquire the element data information and to reduce the calculation time required for the part recognition process.

However, the ultrasound beam S has the smallest width at a focus F1. Therefore, in a case in which the scanning lines L are thinned out in the arrangement direction X, it is difficult to acquire the information of the spatial spreading of the sound waves in the vicinity of both sides of each focus F1 in the arrangement direction X.

Figure 9:
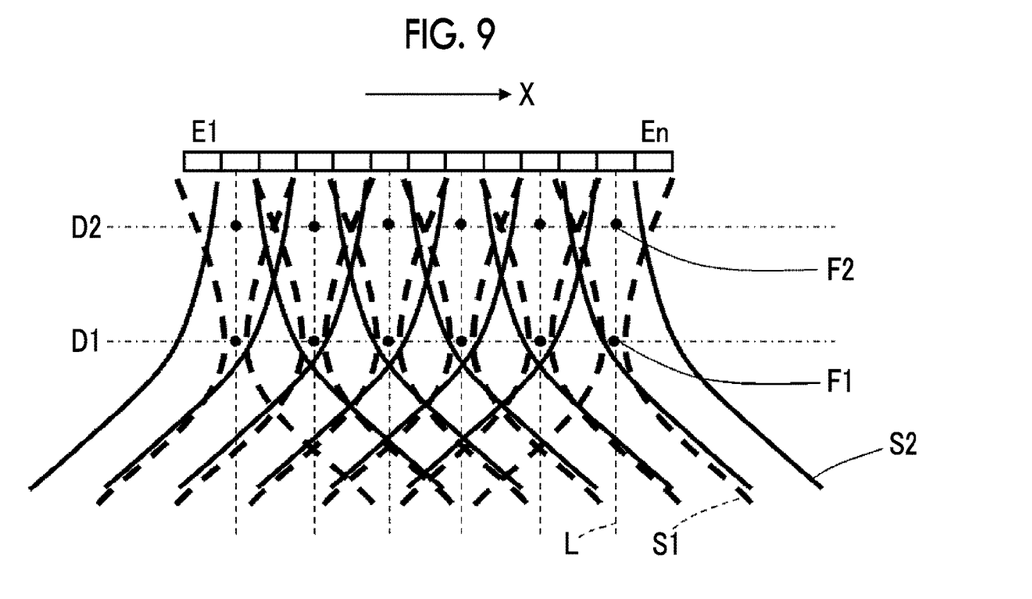
FIG. 9 is a diagram illustrating an aspect in which scanning lines are thinned out in another modification example of Embodiment 1.

For this reason, preferably, as illustrated in FIG. 9, in addition to the focus F1 that is located at a depth D1, a focus F2 that is located at a depth D2 is set on each scanning line L and the plurality of elements E1 to En transmit an ultrasound beam S2 to the focus F2. In a case in which a plurality of focuses are set on the scanning line L, it is possible to acquire the information of the spatial spreading of a larger number of sound waves in a wider range in the arrangement direction X than those in a case in which only one focus is set on the scanning line L. As a result, it is possible to improve the accuracy of part recognition.

In a case in which the focus is not narrowed and an ultrasound beam with a large width is transmitted from the plurality of elements E1 to En, the quality of the B-mode image signal deteriorates, but it is possible to acquire the information of the spatial spreading of the sound waves in a wider range in the arrangement direction X.

In this embodiment, the part recognition unit 13 reads all of the collation patterns from the collation pattern database 16. However, the invention is not limited thereto. For example, in a case in which an extended focused assessment with sonography for trauma (eFAST) examination that continuously examines a plurality of predetermined examination parts is performed, the part recognition unit 13 may be configured so as to read only the collation patterns corresponding to the plurality of predetermined examination parts from the collation pattern database 16. This configuration of the part recognition unit 13 makes it possible to rapidly complete the part recognition process of the part recognition unit 13.

In addition, in a case in which the element data is analyzed to acquire element data information, an error is likely to occur in the acquired element data information in the depth direction and the arrangement direction of the plurality of elements E1 to En, depending on the individual difference between the subjects and a difference in, for example, the body position of the subject in examination. Therefore, in a case in which the part recognition unit 13 collates the element data information using the collation pattern related to the element data information, considering the error, it is preferable to collate the element data information including the periphery of the position of the examination part corresponding to the collation pattern. As such, in a case in which the element data information including the periphery of the examination part corresponding to the collation pattern is collated, it is possible to perform the part recognition process with high accuracy.

Embodiment 2

In Embodiment 1, the element data information is collated using the information of the spatial spreading of the sound waves included in the element data information. However, in Embodiment 2, the element data information is collated using the information of the spatial spreading of the sound waves separated by frequency characteristics.

Figure 10:
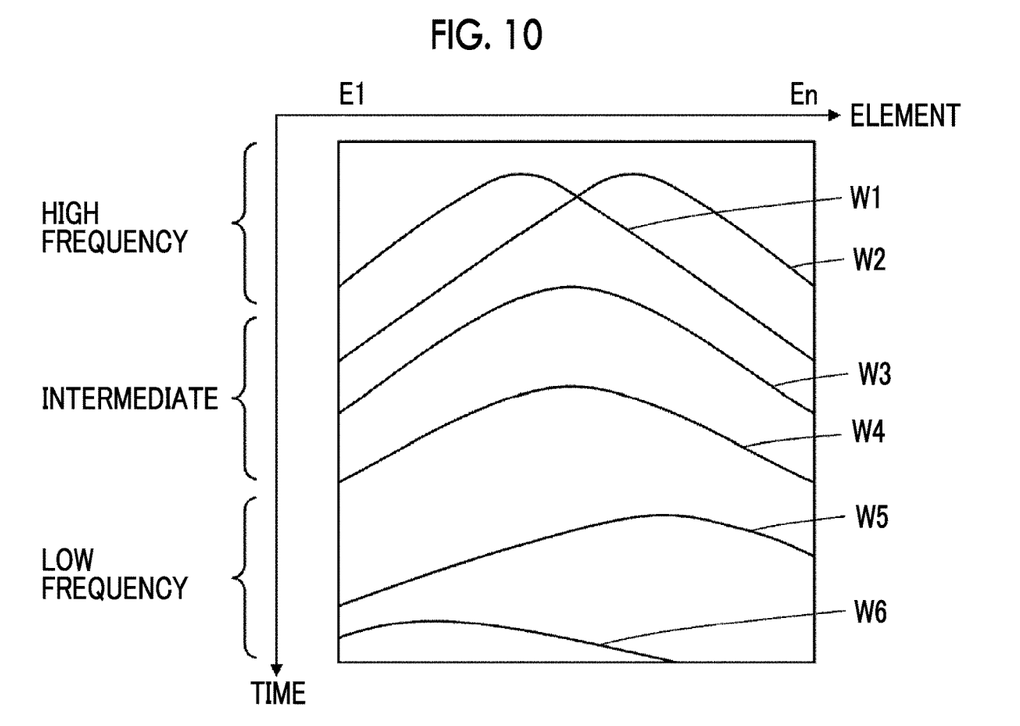
FIG. 10 is a diagram illustrating element data information in Embodiment 2.

FIG. 10 illustrates element data information in Embodiment 2. The element data information includes the information of the spatial spreading of the sound waves separated by frequency characteristics.

In general, a larger number of high-frequency components are lost and a larger number of low-frequency components remain as ultrasonic waves are propagated to a deeper position. For example, in the element data information illustrated in FIG. 10, reflected waves W1 and W2 from a relatively shallow position include a large number of high-frequency components, reflected waves W5 and W6 reflected from a relatively deep position include a large number of low-frequency components, and reflected waves W3 and W4 from an intermediate position between the reflected waves include a large number of intermediate frequency components. That is, the size of each frequency component of each reflected wave changes depending on the position of the reflected wave in the depth direction.

Therefore, a collation pattern including the information of the spatial spreading of the sound waves separated by frequency characteristics may be prepared in advance and the element data information may be collated using the collation pattern. In this case, it is possible to perform part recognition determining from which examination part of the subject the ultrasound echoes have been reflected.

In a case in which the element data analysis unit 12 according to Embodiment 2 analyzes the element data stored in the element data memory 11, for example, the element data analysis unit 12 can perform a process, such as fast Fourier transform, for the element data to analyze frequencies and can divide the element data into the information of the spatial spreading of three-level sound waves, that is, a low-frequency wave, an intermediate wave, and a high-frequency wave. For example, in a case in which the frequency of the driving signal supplied from the transmitting unit 6 of the transmitting/receiving unit 2 to a plurality of elements E1 to En is 7.5 MHz, the high frequency can be set to 6 MHz to 7.5 MHz, the intermediate frequency can be set to 4 MHz to 6 MHz, and the low frequency can be set to less than 4 MHz. In addition, the frequency levels are not limited to three frequency levels, that is, a low frequency, an intermediate frequency, and a high frequency, but may be two frequency levels or four or more frequency levels. Alternatively, the frequency level may continuously change depending on the position where the reflected waves are generated in the depth direction.

The collation pattern of the element data information including the information of the spatial spreading of the sound waves separated by the frequency characteristics in which, for example, the high frequency is set to 6 MHz to 7.5 MHz, the intermediate frequency is set to 4 MHz to 6 MHz, and the low frequency is set to less than 4 MHz is used to collate the element data information. In a case in which the element data information is collated using the collation pattern, it is preferable that the element data information and the collation patterns are separated by the same frequency characteristics. In this case, it is preferable to prepare a plurality of collation patterns corresponding to a plurality of frequencies which are assumed as the frequencies of the driving signals supplied to the plurality of elements E1 to En for the same examination part in advance.

The accuracy of part recognition can be improved by the configuration in which the element data information including the information of the spatial spreading of the sound waves separated by frequency characteristics in addition to the information of the spatial spreading of the sound waves is collated and the part recognition process is performed.

Embodiment 3

In Embodiment 1, the element data information is collated using the information of the spatial spreading of the sound waves included in the element data information. However, in Embodiment 3, element data information is collated using information of the amplitude of the sound waves included in the element data information in addition to the above-mentioned information.

Figure 11:
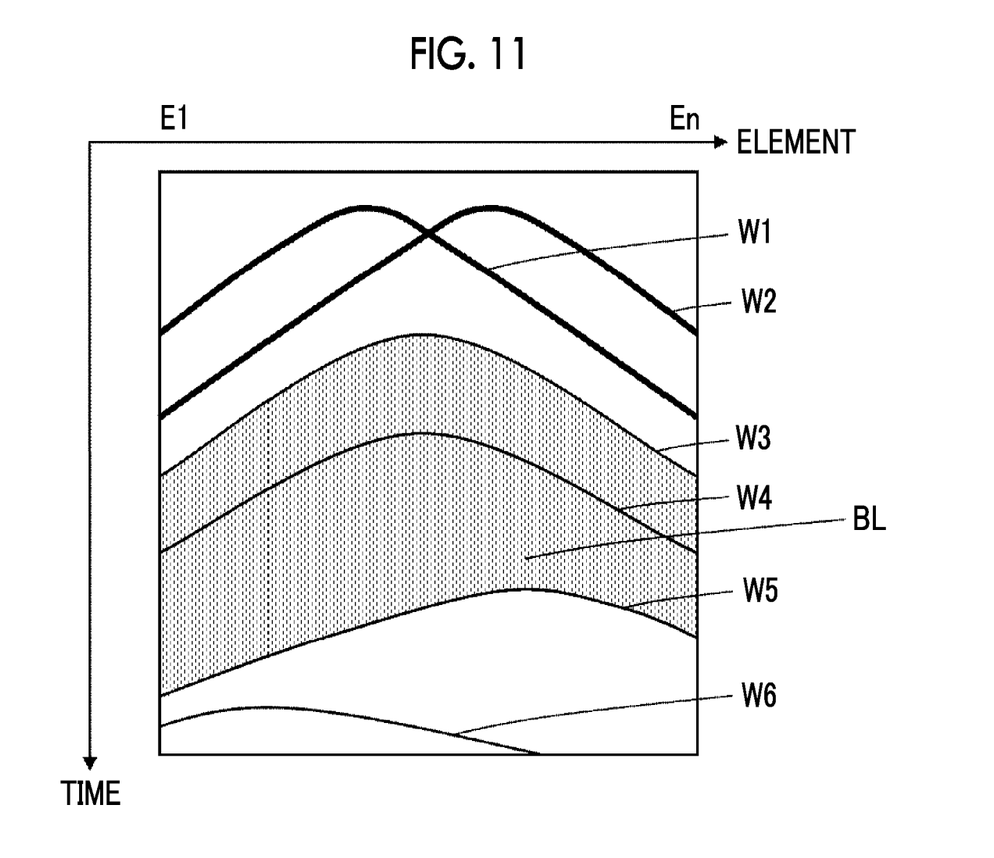
FIG. 11 is a diagram illustrating element data information in Embodiment 3.

FIG. 11 illustrates element data information in Embodiment 3. The element data information includes the information of the amplitude of the sound waves and the information of the spatial spreading of the sound waves.

The values of the amplitudes of reflected waves W1 to W6 illustrated in FIG. 11 change depending on the examination parts from which the reflected waves W1 to W6 are generated. For example, the amplitude of reflected waves generated from the examination parts, such as blood vessels and the bladder, is significantly less than the amplitude of reflected waves generated from other examination parts. In contrast, since the sound waves do not penetrate into bones, the amplitude of reflected waves generated from the bones is significantly greater than the amplitude of the reflected waves generated from other examination parts.

Since the reflected waves W1 and W2 are generated from the bone B illustrated in FIG. 5, the amplitude of the reflected waves W1 and W2 is greater than the amplitude of the other reflected waves W3 to W6. In addition, a region BL surrounded by the reflected wave W3, the reflected wave W5, and the reflected wave W6 indicates reflected waves generated from blood in the heart H. The amplitude of the reflected waves in the region BL is less than the amplitude of other reflected waves W1 to W6 or is so small that it is hardly detected.

Therefore, a collation pattern including the information of the amplitude of the reflected waves and the information of the spatial spreading of the sound waves is created and the element data information is collated using the collation pattern. This configuration makes it possible to perform part recognition determining from which examination part of the subject the ultrasound echoes have been reflected. For example, the average value of the amplitudes of the reflected waves W1 and W2 with particularly large amplitudes which have been generated from the bone B is calculated. In addition, the average value of the amplitude of the region BL with a particularly small amplitude which has been generated from blood in the heart H is calculated. The calculated average value of the amplitudes is compared with a predetermined determination value to determine the degree of similarity between the element data information and the collation pattern related to the element data information.

In a case in which the element data analysis unit 12 according to Embodiment 3 analyzes the element data stored in the element data memory 11, the element data analysis unit 12 can acquire the element data information including the information of the amplitude of the sound waves and the information of the spatial spreading of the sound waves.

The part recognition unit 13 collates the element data information acquired by the element data analysis unit 12 using the collation pattern related to the element data information including the information of the amplitude of the sound waves and the information of the spatial spreading of the sound waves. In this case, it is possible to perform part recognition indicating that the ultrasound echoes have been reflected from an examination part corresponding to the collation pattern from which the average value of the amplitudes closest to the predetermined determination value has been calculated.

As such, the element data information including the information of the amplitude of the sound waves in addition to the information of the spatial spreading of the sound waves is collated and the part recognition process is performed. Therefore, it is possible to improve the accuracy of part recognition.

In addition, the information of the spatial spreading of the sound waves separated by frequency characteristics described in Embodiment 2 and the element data information including the information of the amplitude of the sound waves described in Embodiment 3 may be collated and the part recognition process may be performed. In this case, the amount of information used for part recognition further increases and it is possible to further improve the accuracy of part recognition.

EXPLANATION OF REFERENCES

1: array transducer
2: transmitting/receiving unit
3: image generation unit
4: display control unit
5: display unit
6: transmitting unit
7: receiving unit
8: transmission/reception control unit
9: B-mode processing unit
10: DSC
11: element data memory
12: element data analysis unit
13: part recognition unit
14: imaging condition setting unit
15: apparatus control unit
16: collation pattern database
17: operation unit
18: storage unit
19: amplification unit
20: A/D conversion unit
21: beam former
22: signal processing unit
F, F1, F2: focus
L: scanning line
S, S1, S2: ultrasound beam
P1 to P6: reflection point
W1 to W6: reflected wave
H: heart
C: outer wall of heart
V: boundary between left atrium and left ventricle and right atrium and right ventricle of heart
B: bone
E1 to En, Ej, Ek, Et, Et+1: element
BL: region
D1, D2: depth
X: arrangement direction

What is claimed is:

1. An ultrasound diagnostic apparatus comprising:
   an array transducer in which a plurality of elements are arranged;
   a processor configured
   to transmit an ultrasound beam from the array transducer to a subject;
   to receive ultrasound echoes from the subject using the array transducer to acquire element data; and
   to analyze the element data acquired to acquire element data information that is two-dimensional data information in which the element data obtained from each of the plurality of elements by one ultrasonic wave transmission and reception operation is arranged in a direction in which the plurality of elements are arranged and a reception time direction; and
   a collation pattern database in which a plurality of collation patterns that are associated with a plurality of examination parts of the subject and are related to the element data information are stored in advance,
   wherein the processor reads the collation pattern from the collation pattern database and collates the element data information acquired using the read collation pattern to perform part recognition determining from which examination part of the subject the ultrasound echoes have been reflected.

2. The ultrasound diagnostic apparatus according to claim 1, further comprising:
   an element data memory that sequentially stores the element data acquired,
   wherein the processor analyzes the element data stored in the element data memory to acquire the element data information.

3. The ultrasound diagnostic apparatus according to claim 1,
   wherein the processor generates an ultrasound image of the subject using the element data,
   wherein the processor performs the part recognition and a generation of the ultrasound image in parallel.

4. The ultrasound diagnostic apparatus according to claim 2,
   wherein the processor generates an ultrasound image of the subject using the element data,
   wherein the processor performs the part recognition and a generation of the ultrasound image in parallel.

5. The ultrasound diagnostic apparatus according to claim 3,
   wherein the number of scanning lines corresponding to each element data for acquiring the element data information used for the part recognition is less than the number of scanning lines corresponding to each element data used for the generation of the ultrasound image.

6. The ultrasound diagnostic apparatus according to claim 4,
   wherein the number of scanning lines corresponding to each element data for acquiring the element data information used for the part recognition is less than the number of scanning lines corresponding to each element data used for the generation of the ultrasound image.

7. The ultrasound diagnostic apparatus according to claim 5,
   wherein the scanning lines corresponding to each element data for acquiring the element data information used for the part recognition are thinned out at a predetermined interval in a direction in which the plurality of elements are arranged, with respect to the scanning lines corresponding to each element data used for the generation of the ultrasound image.

8. The ultrasound diagnostic apparatus according to claim 6,
wherein the scanning lines corresponding to each element data for acquiring the element data information used for the part recognition are thinned out at a predetermined interval in a direction in which the plurality of elements are arranged, with respect to the scanning lines corresponding to each element data used for the generation of the ultrasound image.

9. The ultrasound diagnostic apparatus according to claim 3,
wherein the processor sets image generation conditions corresponding to an examination part of the subject recognized,
wherein the processor generates the ultrasound image according to the image generation conditions set.

10. The ultrasound diagnostic apparatus according to claim 5,
wherein the processor sets image generation conditions corresponding to an examination part of the subject recognized,
wherein the processor generates the ultrasound image according to the image generation conditions set.

11. The ultrasound diagnostic apparatus according to claim 7,
wherein the processor sets image generation conditions corresponding to an examination part of the subject recognized,
wherein the processor generates the ultrasound image according to the image generation conditions set.

12. The ultrasound diagnostic apparatus according to claim 9,
wherein the processor further sets ultrasound beam transmission conditions corresponding to the examination part of the subject recognized, and
the processor transmits the ultrasound beam according to the ultrasound beam transmission conditions set.

13. The ultrasound diagnostic apparatus according to claim 10,
wherein the processor further sets ultrasound beam transmission conditions corresponding to the examination part of the subject recognized, and
the processor transmits the ultrasound beam according to the ultrasound beam transmission conditions set.

14. The ultrasound diagnostic apparatus according to claim 11,
wherein the processor further sets ultrasound beam transmission conditions corresponding to the examination part of the subject recognized, and
the processor transmits the ultrasound beam according to the ultrasound beam transmission conditions set.

15. The ultrasound diagnostic apparatus according to claim 1,
wherein the processor further acquires the element data information including information of frequency characteristics.

16. The ultrasound diagnostic apparatus according to claim 1,
wherein the processor further acquires the element data information including information of an amplitude.

17. The ultrasound diagnostic apparatus according to claim 1,
wherein the processor transmits the ultrasound beam to a plurality of different focuses,
the processor acquires each element data information for the plurality of focuses, and
the processor collates each element data information for the plurality of focuses, using the collation pattern.

18. The ultrasound diagnostic apparatus according to claim 17,
wherein the processor analyzes a plurality of element data output from the plurality of elements that have received the ultrasound echoes reflected in the vicinity of each focus to acquire the element data information.

19. A method for controlling an ultrasound diagnostic apparatus, the method comprising:
a step of transmitting an ultrasound beam from an array transducer in which a plurality of elements are arranged to a subject;
a step of receiving ultrasound echoes from the subject using the array transducer to acquire element data;
a step of analyzing the acquired element data to acquire element data information that is two-dimensional data information in which the element data obtained from each of the plurality of elements by one ultrasonic wave transmission and reception operation is arranged in a direction in which the plurality of elements are arranged and a reception time direction; and
a step of collating the element data information using a plurality of collation patterns that are associated with a plurality of examination parts of the subject to perform part recognition determining from which examination part of the subject the ultrasound echoes have been reflected.

* * * * *